United States Patent
Methfessel

[11] Patent Number: 6,049,082
[45] Date of Patent: Apr. 11, 2000

[54] METHOD AND INSTRUMENT COMBINATION FOR PRODUCING COMPARABILITY OF SPECTROMETER MEASUREMENTS

[75] Inventor: Jennifer Methfessel, Frankfurt an der Oder, Germany

[73] Assignee: Bran + Luebbe GmbH, Norderstedt, Germany

[21] Appl. No.: 08/945,929

[22] PCT Filed: Dec. 20, 1996

[86] PCT No.: PCT/EP96/05779

§ 371 Date: Aug. 26, 1997

§ 102(e) Date: Aug. 26, 1997

[87] PCT Pub. No.: WO97/24605

PCT Pub. Date: Jul. 10, 1997

[30] Foreign Application Priority Data

Dec. 27, 1995 [DE] Germany .................. 195 48 378

[51] Int. Cl.[7] .................. G01J 3/42; G01J 3/28
[52] U.S. Cl. .................. 250/339.09; 356/300; 356/326; 356/319
[58] Field of Search .................. 250/339.09; 356/300, 356/326, 319

[56] References Cited

U.S. PATENT DOCUMENTS 5,132,538  7/1992  Norris .

FOREIGN PATENT DOCUMENTS

| 0 345 773 | 12/1989 | European Pat. Off. . |
| 25 09 091 | 9/1976 | Germany . |
| 39 08 831 A1 | 9/1989 | Germany . |
| WO 95/01348 | 3/1985 | WIPO . |

*Primary Examiner*—Constantine Hannaher
*Assistant Examiner*—Andrew Israel
*Attorney, Agent, or Firm*—Michael J. Striker

[57] ABSTRACT

A method provides the comparability of spectrometer measurements with a plurality of measuring instrument individuals of the same type in a family, and a spectrometer for performing the method is used with automatic standardization is also described. By this method and with this spectrometer, a substantial improvement in comparability as well as accuracy of spectral measurements is possible, since the measurement values are replicable by means of a calibration of the spectrometers, and varying consistencies or dimensions among specimens are balanced out or compensated for.

16 Claims, 1 Drawing Sheet

METHOD AND INSTRUMENT COMBINATION FOR PRODUCING COMPARABILITY OF SPECTROMETER MEASUREMENTS

BACKGROUND OF THE INVENTION

The invention relates to a method and combination of devices for providing the comparability of spectrometer measurements, preferably in the near infrared range, with a plurality of measuring instrument individuals of the same type in a family.

NIR spectrometers have gained wide application. They are used to analyze gaseous and solid substances. With constantly increasing demands for accuracy, exact calibration of these instruments gains particular significance. It is especially important that the measured values of a specimen obtained with one spectrometer be replicable on another spectrometer of the same type.

Moreover, the accuracy of the spectral measurements is impaired by changes in the specimen being measured itself, for instance with regard to its consistency or dimensions in the case of nonhomogeneous materials. A standardizing method for reducing particle size effects is described for instance in U.S. Pat. No. 5,132,538.

It is well known to use natural (absolute) standards for standardizing the measuring instruments, among them for instance using a spectral absorption band of a gas to calibrate the wavelength scale of a spectrometer. In the field of infrared and near infrared spectroscopy, the standardization of the wavelength scale in this way is state of the art. On the other hand, the scale for the intensity is not standardized. Specimens are measured relative to a "hundred percent" standard specimen or reference. In measurements of reflection, this typically means a "hundred percent" reflector. In measurements of transmission, this typically means the signal magnitude at which there is no specimen in the beam of light. In addition, the "zero signal" can be measured by physically preventing the beam of light from reaching the detector. The signal of the specimen can then be corrected by means of the offset signal measured.

It is assumed of the signals $S_s$ and $S_r$ already corrected with the measured offset signal, it is assumed that $S_s/S_r$ is directly proportional to $I_s/I_r$;

$S_s$ means the signal when the specimen is measured;

$S_r$ means the signal when the reference is measured;

$I_s$ means the true signal for the light intensity that is reflected by the specimen or transmitted through the specimen;

$I_r$ is the true signal for the intensity of the light that is reflected or transmitted by the reference.

In fact, the design of spectrometers takes this circumstance particularly into effect by designing the detectors in such a way that they are operated in the linear range of their characteristic curve. As much as possible, the user must then make sure that $I_s$ and $I_r$ are measured under the same peripheral conditions. Many cases exist, however, in which spectrometers of the state of the art, operated in the way described above, fail in measuring an intrinsically correct signal for the reflection or transmission of a given specimen. The differences in spectral sensitivity (on the scale of intensity) between spectrometer individuals can be very great, even in those of the same family. In some cases, the sensitivity of spectrometers is directly proportional to $I_s/I_r$, but the linearity coefficients of the instruments differ from one another. In other cases, $S_s/S_r$ is linked in a more-complex way to $I_s/I_r$, namely nonlinearly.

The reasons why the linearity coefficients between the instruments vary may be differences in the reflection from the reference specimen, differences in the optical adjustment, mechanical tolerances of the specimen holder, and so forth.

The reason for the nonlinear relationship between $S_s/S_r$ and $I_s/I_r$ may be a nonlinear detector characteristic curve, or scattered light, which depends on the reflection (transmission) of the specimen. Another reason for the nonlinearity may be multiple reflections at optical boundary layers because of great differences in the index of refraction. The nonlinear effects occur especially markedly at the point of contact with the specimen and are amplified even more if sapphire (index of refraction n=1.75) is used as window material instead of quartz (n=1.45), for instance. In many applications, however, sapphire windows are necessary, for instance because of their superior strength and resistance. It is therefore the object of the invention to improve the accuracy and replicability attainable for a number of spectral measurements of the same type.

SUMMARY OF THE INVENTION

This object is attained by a method of the type referred to at the outset, which is distinguished by the following method steps:

storage in memory of set-point spectra of immobilized standard specimens in a spectrometer individual of the family;

ascertaining a number of comparison spectra of the standard specimens with the spectrometer individual of the family;

calculating parameters of an approximation for the deviation in the comparison spectrum from the set-point spectrum per wavelength base point on the standard specimens;

storage in memory of the parameters per wavelength base point in the instrument;

measurement of the spectrum of an unknown specimen;

calculation of true values for each wavelength base point of a measured value of the spectrum of the unknown specimen, using an equation that is obtained from the approximation function;

outputting of the corrected spectrum as an actual spectrum.

Accordingly, the method links together instruments and a set of standard specimens for evaluating measurements and the calculation of parameters for the correction. One advantage of this method is that it is independent of any particular mother instrument, since it is based on absolute diffuse reflectances or absorptances, which are derived from a standard. The mother system can be replaced or duplicated at any time.

The method is also suitable for all types of spectroscopic measurements, that is, transmission, reflection or absorption measurements, if the standard specimens are defined in a suitable way. The standard specimens must cover the relevant measuring range and must have stable physical properties.

In an advantageous embodiment of the method, eight standard specimens are provided, for instance with diffuse reflectances of 2%, 5%, 10%, 20%, 40%, 50%, 60%, 80%, and 99%.

Technical factors having to do with the instruments themselves can be precluded by providing that the approximation function is of at least second or higher order.

The accuracy of later measurements of unknown specimens is further improved by providing that at least three measurements of comparison spectra per reflectance are performed, whose values are preferably averaged for each wavelength base point.

For calculating the parameters of the approximation function per wavelength base point, it is provided that the spectra of the specimens with different reflectances are used to calculate parameters of the approximation function.

The provision that the quality of the approximation function is determined by calculating the standard deviation or the correlation coefficient at each wavelength base point makes it possible to monitor the results of measurement for reliability at any time.

The object is also attained by a spectrometer for performing the method in that it has a first memory for a plurality of set-point spectra and a second memory for comparison spectra of different standard specimens, from the comparison of the spectra for each wavelength base point, the parameters of the approximation function can be determined.

To that end, it is provided that it has a unit for calculating parameters of an approximation function for each wavelength base point by comparison of the comparison spectra with the set-point spectra of the standard specimens.

Once the values or parameters have been found, they are permanently available to the instrument, since it is provided that it has a third memory for parameters for each wavelength base point of an approximation function.

The actual measurement and the processing of the measured values can be done independently of one another, because it has a fifth memory for storing a spectrum of an unknown specimen.

The ascertainment of a "true" spectrum of an unknown specimen is done automatically, because it has an arithmetic unit for calculating actual values by means of an equation determined by the approximation function per wavelength base point of an unknown specimen.

The reliability of the measurement and of the instrument can be monitored at any time, because it has an arithmetic unit for calculating the quality of the approximation function.

For outputting the corrected "true" spectrum as an actual spectrum, an output unit is provided.

Because the spectrometer is assigned a set of standard specimens, which are furnished for providing the comparability of spectrometer measurements of the spectrometers, the measurements of an entire family of instruments of the same type can be compared with one another.

If it has a memory-programmable controller for performing the method, then the method proceeds without external intervention. The individual steps in the method are stored in the program memory of the controller.

The method prevents different sensitivities among the instruments from having any influence. The differences in composition or dimensions of the specimen are intrinsically not taken into account by this method or by the spectrometer. It is therefore provided in an advantageous embodiment that the specimens for instruments of the same type are received in a holder of identical dimensions, and the holder is preferably indexed so that changes in length are also averted.

Further details, characteristics and advantages of the invention will become apparent from the ensuing description in conjunction with the drawing.

BRIEF DESCRIPTION OF THE DRAWING

The sole drawing FIGURE is a block circuit diagram of a device according to the invention for performing the method.

DESCRIPTION OF PREFERRED EMBODIMENTS

Figure 1:
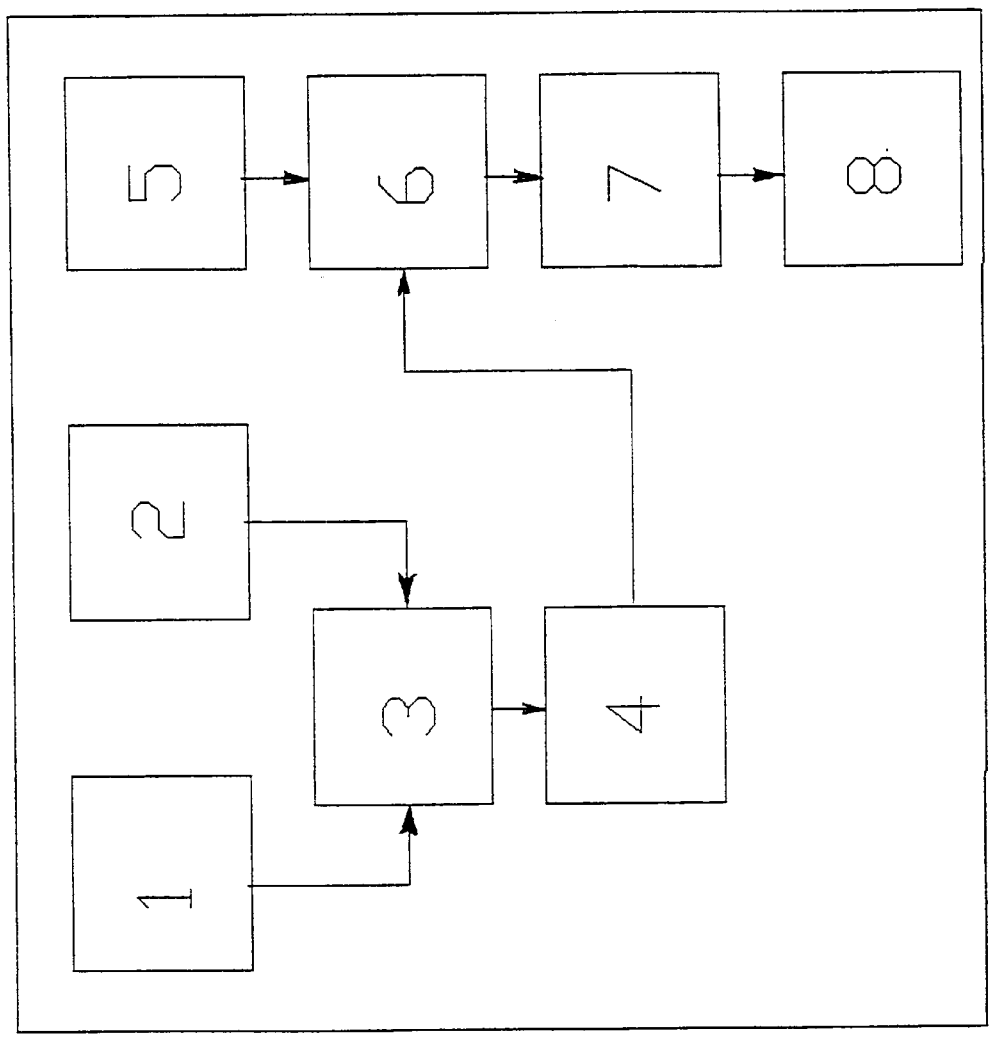

The drawing shows a block circuit diagram of a device for performing the method, in which a quadratic function, which assumes a nonlinear dependency, is provided as the approximation function. The device has one memory 1 for set-point spectra and one memory 2 for comparison spectra. In an arithmetic unit 3, one set of parameters, which represent the coefficients of the approximation functions, for each wavelength base point is calculated by comparing the comparison spectra with the set-point spectra of the standard specimens. The values of the parameters are stored in a memory 4. A memory 5 is also present for storing the spectrum of an unknown specimen. With an arithmetic unit 6, one actual value is calculated, then deposited in the memory 7, and finally by means of an output device 8, the corrected spectrum is output as an actual spectrum.

The method for standardization described below has been developed for measurements with diffuse reflection, which use a near infrared spectrometer with a fiber optical sensor. The guard window at the tip of a fiber optical sensor is made of corundum. During the measurement, the window is in contact with the specimen or very close to the specimen (distance approximately 0.1 mm). In this case, the dependency between $S_s/S_r$ and $I_s/I_r$ can be well described by a quadratic equation, since multiple reflections at the boundary face between corundum and reflector contribute to a notable quadratic component.

For performing the method, first eight standard specimens with diffuse reflection of 2%, 5%, 10%, 20%, 40%, 50%, 60%, 80%, and 99% are measured on the spectrometer. This produces eight spectra of diffuse reflection as a function of the wavelength (approximately 450 data points). The measurement of the eight standard specimens is repeated three times. Before each new measurement series, the reference is measured anew.

The three spectra of diffuse reflection are averaged and smoothed for each value, using a Savitsky-Golay algorithm. These averaged and smooth spectra are the "measured" values of the standard specimens.

The eight standard specimens have previously been measured during a reference instrument. The measurements on that instrument make eight spectra of diffuse reflection over the wavelength available. These are the "true" values.

For each wavelength (i), there are eight "measured" values and eight "true" values. For an ideal spectrometer, the "true" values would be identical to the "measured" values. However, because of a number of factors that have been discussed above, this is not the case. In the case being observed here, the relationship between the "measured" values and the "true" values can be correctly described by the following quadratic function:

$$Y(i) = A \cdot X(i)^2 + B \cdot X(i) + C \qquad (1)$$

In the equation, A is the quadratic coefficient, B the linear coefficient, and C the constant zero point deviation (offset). The coefficients are the parameters of the approximation function. Y is given as a function of X, since it is assumed of Y, or of the "measured" values, that they have a greater experimental error.

The software calculates the coefficients for the best quadratic approximation between the "measured" values and the "true" values, using the method of least square deviation.

As soon as the parameters of the approximation function, that is, A, B and C, are known, equation 1 can be used to calculate the X (i) values, as a function of the Y (i) values. These are the "corrected measured" values, since they have been adapted in such a way that they take into account the influence of the spectral characteristics of the spectrometer. Equation 1 is converted into the following form:

$$X(i)^2 + p \cdot X(i) + q = 0 \qquad (2)$$

in which
p=B/A and q=[C−Y(i)]/A.
By taking the root from equation (2), one obtains:

$$X_1(i) = -p/2 + \sqrt{(p/2)^2 - q} \qquad (3)$$

and $$X_2(i) = -p/2 - \sqrt{(p/2)^2 - q} \qquad (4)$$

The root that is of interest for the present problem is the one that is located closest to the actual value to be expected. If a corundum window is used, this is usually the root indicated in equation (3). However, cases can arise for instance where the fiber optics are used without a window, as a result of which the root given in equation (4) is the correct one. Both root expressions are therefore calculated. Typically, the value of one root is between 0 and 1, while the value of the other roots is higher by a factor of 10.

The quality of the quadratic approximation is monitored by plotting the "true" values for each wavelength by way of the "corrected measured" values and performing a linear regression. A perfect approximation would yield a correlation coefficient having the value 1.

Another method for ascertaining the quality of the quadratic approximation is to calculate the standard deviation of the error in reflection (SER) for each wavelength, which is defined as the standard deviation of the residual error between the "true" values and the "corrected measured" values.

The software calculates the correlation coefficient and the standard deviation in the reflection for each wavelength. The quality of the quadratic approximation is ascertained only in the normal operating range of the spectrometer. For the standardization, the quadratic approximation is considered to be sufficiently good if the average of the correlation coefficient over all the wavelengths is greater than or equal to 0.9995, and the least correlation coefficient is greater than or equal to 0.9990. In a similar way, the SER should be less than or equal to 0.001 reference units. These limits have been ascertained experimentally by experiments, using a number of spectrometers in the same family and a number of standardized sets of standard specimens. The limits thus indicate the desired extent of standardization in this case.

As soon as these conditions have been met, the software for producing the comparability is started. All the following measurements are corrected automatically, by using equations 3 or 4, in order to indicate the "true" values. The measurements that are performed on the spectrometer now correspond to the measurements that were obtained on the reference instrument, with a residual error, which corresponds to the accuracy of the approximation, or that is due to noise components, etc. The same method can be repeated using an arbitrary number of spectrometers, thus achieving a population of standardized spectrometers.

The significance of the reference instrument and of the set of reference specimens will now be described. The reference instrument is produced by using a set of reference specimens. This set of reference specimens comprises eight diffuse-reflection targets, which cover the range between 2% and 99% and have been calibrated on a spectrometer that was in turn calibrated with specimens certified by the national calibration agency, such as the National Bureau of Standards in the United States. The values for the diffuse reflection that are measured are therefore absolute properties of the material. These values represent the "true" values of the set of standard specimens.

The diffuse-reflecting specimens are now secured in individual holders, so that they are available in a replicable way to the reference instrument. This is the set of standard reference specimens.

The set of standard reference specimens is now measured, as described above, on the reference instrument. As before, the quadratic and linear coefficients and the offset in the quadratic approximations are calculated for each wavelength. The correlation coefficient and the standard error in reflection are needed once again in order to ascertain the quality of the approximation and to determine the residual error in the operating wavelength range of the spectrometer. These same criteria are used for the decision whether the quadratic approximation is good enough to use it for the standardization.

Once the method for producing the comparability is completed, the measurement values that were performed on the reference instrument correspond to those that were ascertained by the national calibration agency, within the limits of the residual error, which is estimated at ±0.01 reference units (standard deviation).

The comparability with standards and measurements of the national calibration agency is thus achieved.

As soon as the reference instrument has once been standardized in this way, it can be used to ascertain the "true" values directly for further sets of standard specimens.

The advantage of this method is that it is independent of a fixed set of reference specimens or of one reference instrument, because the method is based on the absolute diffuse reflection that has been certified by the national calibration agency. Both the reference instrument and the set of reference specimens can be replaced at any time or duplicate it at any time.

The production of comparability is a method that makes it possible to standardize various spectrometers of the same family, by using the absolute property of a special standardized material and suitable computation methods, as described above.

The same method for standardization can be employed with any type of spectroscopic measurements, such as reflection, transmission or transflection, on the condition that a set of suitable standard specimens can be defined. The set of standard specimens must cover the relevant measurement range and must incorporate an invariant physical property. This physical property must be quantifiable by means of an independent body.

The relationship between the "measured" values and the "true" values will differ among different constructions of spectrometers. It can therefore be appropriate for the quadratic equations used here to be replaced either by a simple linear equation or by equations of a higher order. If the equations cannot be analytically solved, then other numerical methods can be used. The number of standard specimens used can be adapted to the complexity of the relationship and to the requisite accuracy.

I claim:

1. A method for providing the comparability of spectrometer measurements, in particular for measurements with diffuse reflection, using a plurality of measuring instrument individuals of the same type in one family, characterized by the following method steps:

storage in memory of set-point spectra or immobilized standard specimens in a spectrometer individual of the family;

ascertaining a number of comparison spectra of the standard specimens with the spectrometer individual of the family;

calculating parameters of an approximation for the deviation in the comparison spectrum from the set-point spectrum per wavelength base point on the standard specimens;

storage in memory of the parameters per wavelength base point in the instrument;

measurement of the spectrum of an unknown specimen;

calculation of true values for each wavelength base point of a measured value of the spectrum of the unknown specimen, using an equation that is obtained from the approximation function, which is at least second or higher order.

2. The method for providing the comparability of spectrometer measurements, in accordance with claim 1, characterized in that a plurality of standard specimens, in particular more than seven specimens, are used, with diffuse straight reflectances of 2%, 5%, 10%, 20%, 40%, 50%, 60%, 80%, and 99%.

3. The method for providing the comparability of spectrometer measurements, in accordance with claim 1, characterized in that at least three measurements of comparison spectra per reflectance are performed, whose values are averaged for each wavelength base point.

4. The method for providing the comparability of spectrometer measurements, in accordance with claim 1, characterized in that the quality of the approximation function is determined by calculating the standard deviation or the correlation coefficient at each wavelength base point.

5. A spectrometer for measuring spectra for using the method in accordance with claim 1, 2, 3, or 4, characterized in that it has a first memory (1) for a plurality of set-point spectra, a second memory (2) for comparison spectra of different standard specimens, and means for calculation of true values for each wavelength base point of a measured value of the spectrum of the unknown specimen using an equation that is obtained from the approximation function of at least second or higher order.

6. A spectrometer for measuring spectra in accordance with claim 5, characterized in that it has a unit (3) for calculating parameters of an approximation function for each wavelength base point by comparison of the comparison spectra with the set-point spectra of the standard specimens.

7. A spectrometer for measuring spectra in accordance with claim 5, characterized in that it has a third memory (4) for parameters for each wavelength base point of an approximation function.

8. A spectrometer for measuring spectra in accordance with claim 5, characterized in that it has a fifth memory (5) for storing a spectrum of an unknown specimen.

9. A spectrometer for measuring spectra in accordance with claim 5, characterized in that it has an arithmetic unit (6) for calculating actual values by means of an equation determined by the approximation function per wavelength base point of an unknown specimen.

10. A spectrometer for measuring spectra in accordance with claim 5, characterized in that it has an arithmetic unit (6) for calculating the quality of the approximation function.

11. A spectrometer for measuring spectra in accordance with claim 5, characterized in that it has an output unit (8) for outputting the corrected spectrum as an actual spectrum.

12. A spectrometer for measuring spectra in accordance with claim 5, characterized in that the spectrometer is assigned a set of standard specimens, which are furnished for providing the comparability of spectrometer measurements of the spectrometers.

13. A spectrometer for measuring spectra in accordance with claim 5, characterized in that it has a memory-programmable controller for performing the method.

14. A method for providing the comparability of spectrometer measurements, in particular for measurements with diffuse reflection, using a plurality of measuring instrument individuals of the same type in one family, characterized by the following method steps:

storage in memory of set-point spectra or immobilized standard specimens in a spectrometer individual of the family;

ascertaining a number of comparison spectra of the standard specimens with the spectrometer individual of the family;

calculating parameters of an approximation for the deviation in the comparison spectrum from the set-point spectrum per wavelength base point on the standard specimens;

storage in memory of the parameters per wavelength base point in the instrument;

measurement of the spectrum of an unknown specimen;

calculation of true values for each wavelength base point of a measured value of the spectrum of the unknown specimen, using an equation that is obtained from the approximation function, and the spectra of the specimens with different reflectances per wavelength base point are used to calculate parameters of the approximation function.

15. A spectrometer for measuring spectra for using the method in accordance with claim 1, 2, 3, 4, or 14, characterized in that it has a first memory (1) for a plurality of set-point spectra, a second memory (2) for comparison spectra of different standard specimens, and means for calculation of true values for each wavelength base point of a measured value of the spectrum of the unknown specimen using an equation that is obtained from the approximation function, and using the spectra of the specimens with different reflectances per wavelength base point to calculate parameters of the approximation function.

16. A spectrometer for measuring spectra for using the method in accordance with claim 1, 2, 3, 4, or 14, characterized in that it has a first memory (1) for a plurality of set-point spectra, a second memory (2) for comparison spectra of different standard specimens, and the specimens for instruments of the same type are received in a holder of identical dimensions, and the holder is indexed so that changes in length are also averted.

\* \* \* \* \*